United States Patent [19]

Bargiotti et al.

[11] Patent Number: 4,839,346
[45] Date of Patent: Jun. 13, 1989

[54] ANTITUMOR ANTHRACYCLINE GLYCOSIDES, INTERMEDIATES THEREOF, AND COMPOSITION AND USE THEREOF

[75] Inventors: Alberto Bargiotti; Teresa Bordoni, both of Milan; Pierangelo Zini, Cesano Boscone; Sergio Penco, Milan, all of Italy

[73] Assignee: Farmitalia Carlo Erba S.p.A., Milan, Italy

[21] Appl. No.: 101,382

[22] Filed: Sep. 28, 1987

[30] Foreign Application Priority Data

Oct. 15, 1986 [GB] United Kingdom ............... 8624687

[51] Int. Cl.$^4$ .................... A61K 31/70; C07H 15/24
[52] U.S. Cl. ............................ 514/34; 536/6.4
[58] Field of Search ...................... 536/6.4; 514/34

[56] References Cited

U.S. PATENT DOCUMENTS

| | | | |
|---|---|---|---|
| 4,039,663 | 8/1977 | Arcamone et al. | 536/6.4 |
| 4,562,177 | 12/1985 | Horton et al. | 536/6.4 |
| 4,563,444 | 1/1986 | Angelucci et al. | 536/6.4 |

FOREIGN PATENT DOCUMENTS 2050364  1/1981  United Kingdom ............... 536/6.4

OTHER PUBLICATIONS

Cram et al., *Organic Chemistry*, 2nd ed., 1964, p. 526.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

New anthracycline glycosides having formula:

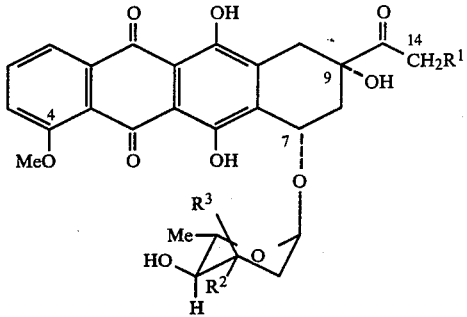

wherein $R^1$ is hydrogen or hydroxy and either $R^2$ or $R^3$ is hydrogen with the other amino-methyl are described. The new compounds and their pharmaceutically acceptable addition salts are useful as antitumour agents.

8 Claims, No Drawings

ANTITUMOR ANTHRACYCLINE GLYCOSIDES, INTERMEDIATES THEREOF, AND COMPOSITION AND USE THEREOF

The invention relates to new anthracyclines, to process for their preparation, to pharmaceutical compositions containing them and to new protected aminosugars used as intermediates in their preparation.

The invention provides the novel anthracycline glycosides IA-D, and their pharmaceutically acceptable addition salts:

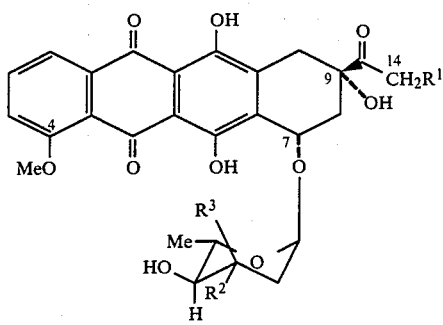

IA: $R^1 = R^2 = H$; $R^3 = CH_2NH_2$
B: $R^1 = OH$; $R^2 = H$; $R^3 = CH_2NH_2$
C: $R^1 = R^3 = H$; $R^2 = CH_2NH_2$
D: $R^1 = OH$; $R^3 = H$; $R^2 = CH_2NH_2$

The glycosides IA and IC are prepared by coupling daunomycinone, a know aglycone of the antitumor anthracycline daunorubicin, with reactive protected derivatives of the new aminosugars 2,3,6-trideoxy-3-aminomethyl-L-ribohexopyranose (IIA) and 2,3,6-trideoxy-3-aminomethyl-L-arabinohexopyranose (IIB) under conditions described in U.S. Pat. No. 4,098,798.

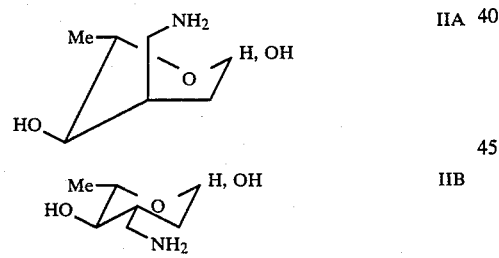

The analogues IB and ID are obtained by bromination of IA and IC respectively, followed by hydrolysis of the 14-bromo-derivatives, preferably according to the method described in U.S. Pat. No. 4,112,076.

Accordingly, the present invention provides a process for the preparation of an anthracycline glycoside of formula (I) or a pharmaceutically acceptable salt thereof, which process comprises:

(i) reacting daunomycinone with a reactive derivative of 2,3,6-trideoxy-3-aminomethyl-L-ribohexopyranose or -L-arabinohexopyranose wherein the amino and 4-hydroxy groups are protected and removing the protecting groups from the product thus-obtained such as to obtain an anthracycline glycoside of formula (I) wherein $R^1$ is hydrogen;

(ii) if desired, converting the said glycoside of formula (I) into a pharmaceutically acceptable salt thereof;

(iii) if desired, brominating the said glycoside of formula (I) or pharmaceutically acceptable salt thereof and hydrolysing the 14-bromo derivative thus obtained so as to from the corresponding glycoside of formula (I) wherein $R^1$ is hydroxy; and (iv) if desired, converting the said glycoside of formula (I) wherein $R^1$ is hydroxy into a pharmaceutically acceptable salt thereof.

The preparation of the anthracycline glycosides of the invention and their salts will now be described in more detail, more specifically in relation to the preparation of first intermediates 5 and 6.

Two synthetic processes have been devised in order to obtain 5 and 6. The first route, shown in Scheme I below, is based on the addition of nitromethane to the known 3-keto sugar 1, affording the nitroderivative 2, from which following the indicated reaction sequence a mixture of 5 and 6 is obtained with preponderant formation of the sugar with L-ribo configuration (5:6=3:1).

SCHEME 1

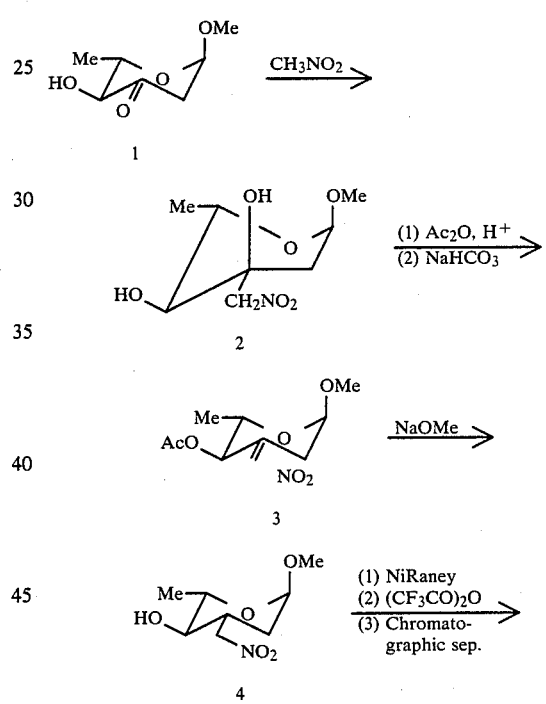

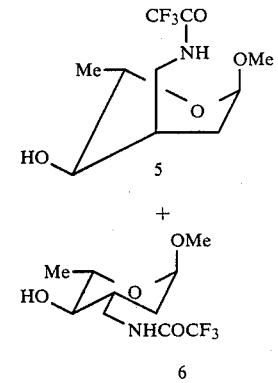

More particularly, the addition of nitromethane in the presence of sodium methoxide affords the corresponding nitroalcohol 2 in 85% yield after crystallization. The nitroene 3, obtained easily from 2, undergoes a reported rearrangement of the double bond in basic conditions to give the unsaturated nitrosugar 4. This when reduced in presence of NiRaney, affords a mixture of the two aminosugars 5 and 6 separated by chromatography as N-trifluoroacetyl derivatives.

An alternative route, shown in Scheme II below, the new amino sugar. Alternatively, the oxidation of 9 to 12, followed by an alkaline treatment, provides the intermediate 13 with the arabino configuration. Intermediate 13 is reduced to alcohol 14. Alcohol 14, following the same reaction sequence used for the conversion of 9 to 5, is converted into the N-protected aminosugar 6 with the L-arabino configuration.

SCHEME II

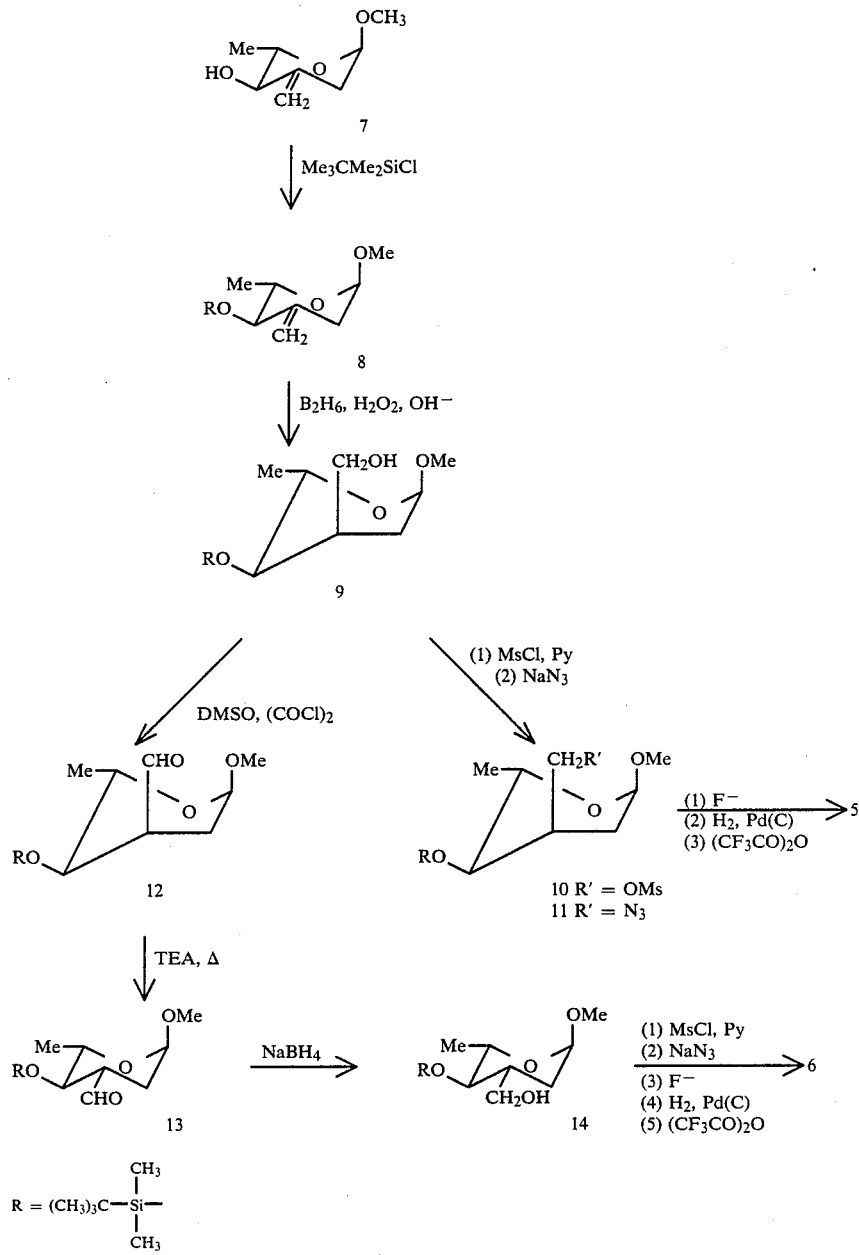

allows intermediates 5 or 6 to be obtained stereoselectively and is based on the use as the key intermediate of the known exocyclic olefine 7 (R. M. Giuliano, Carbohydr. Res. 131 (1984) 341–345) which is easily prepared from 1. The hydroboration of 7 affords the corresponding alcohol 9 stereoselectively. This intermediate allows intermediate 5 to be prepared via formation of the corresponding azide, hydrolysis of the O-protecting group, reduction and finally N-trifluoroacetylation of The preparation of the daunorubicin analogs IA and IC is performed by reacting daunomycinone with 1-chloro-N,O-trifluoroacetyl derivatives IIIA or IIIB, obtained by treatment

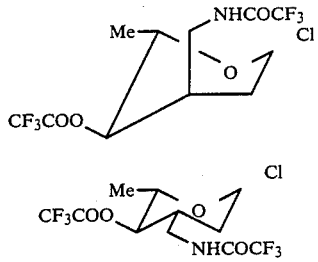

of 5 or 6 with trifluoroacetic anhydride followed by reaction with dry hydrogen chloride. The obtained protected glycoside, following removal of the N-trifluoroacetyl protecting group by mild alkaline hydrolysis, is converted into the new anthracycline IA or IC. This anthracycline can, if desired, be isolated as the hydrochloride. This is typically effected by treating the glycoside with a methanolic solution of hydrogen chloride and isolating the glycoside as its hydrochloride.

The preparation of the doxorubicin analogs IB and ID is performed by brominating IA or IC, for example with bromine in methylene dichloride, to obtain the 14-bromo derivative from which, after hydrolysis typically with an aqueous solution of sodium formate, the new glycoside IB or ID is obtained. Again, the new glycoside can be isolated as the hydrochloride. This is typically effected by treating the glycoside with a methanolic solution of hydrogen chloride and isolating the glycoside as its hydrochloride.

The present invention also provides a pharmaceutical composition comprising as active ingredient an anthracycline glycoside of formula IA-D or a pharmaceutically acceptable salt thereof together with a pharmaceutically acceptable carrier or diluent. Conventional carriers may be used and the composition may be formulated in conventional manner.

The compounds of the invention are useful in methods of treatment of the human or animal body by therapy. In particular the compounds of the invention are useful as antitumor agents by administering a therapeutically effective amount of the compound to a patient.

The following Examples illustrate the invention.

EXAMPLE 1

Preparation of methyl-2,6-dideoxy-3-C-nitromethyl-α-L-ribohexopyranoside (2)

A 1 molar solution of sodium methoxide in methanol (20 ml, 20 mmoles) was added dropwise with stirring to a solution of methyl 2,6-dideoxy-α-L-erythro-hexopyranosid-3-ulose (1) (g 1.60, 10 mmoles) in 70 ml of dry nitromethane.

The reaction mixture was stirred overnight at room temperature and then was deionized with Dowex 50WX8 (H+) resin and the filtrate was evaporated to a solid.

Fraction crystallization of the product from ether gave g 1.66 (75%) of methyl 2,6-dideoxy-3-C-nitromethyl-α-L-ribo-hexopyranoside (2).

m.p. 115° C., $[\alpha]_D^{20} = -104.25$ (c=1, CH$_2$Cl$_2$)

The P.M.R. spectrum (200 MHz, CHCl$_3$) showed absorption at:

1.35 (d, J=6.2 Hz, 3H, CH$_3$- 5), 2.01 (dd, J=3.7, 15.0 Hz, 1H, H-2ax), 2.24 (bd, J=11.7 Hz, 1H, OH-4), 2.32 (dd, J=1.1, 15.0 Hz, 1H, H-2e), 3.06 (dd, J=9.3, 11.7 Hz, 1H, H-4), 3.38 (s, 3H, OCH$_3$), 3.70 (qd, J=6.2, 9.3 Hz, 1H, H-5), 4.26 (d, J=1.5 Hz, 1H, OH-3), 4.34 (dd, J=1.5, 11.1 Hz, 1H, CH(H)—NO$_2$)), 4.74 (d, J=11.1 Hz, 1H, CH(H)—NO$_2$), 4.84 (dd, J=1.1, 3.7 Hz, 1H, H-1)δ.

The $^{13}$C-NMR (50 MHz, CDCl$_3$) showed absorption at: 17.8 (CH$_3$-5); 36.7 (C-2); 55.3 (OCH$_3$); 65.1 (C-5); 71.5 (C-3); 73.5 (C-4); 80.8 (CH$_2$NO$_2$); 97.7 (C-1).

EXAMPLE 2

Preparation of methyl 3-nitromethyl-2,3,6-trideoxy-hex-2-enopyranoside (4)

Compound (2) (g 1.1, 5 mmoles) was treated with 70 ml of acetic anhydride and 0.7 g of p-toluensulfonic acid monohydrate at room temperature overnight.

The reaction mixture was poured into ice-water and treated with sodium hydrogen carbonate under stirring.

After neutralization the mixture was allowed to warm up to room temperature with stirring and extracted with ethyl acetate.

The organic extract was washed with water, then dried over sodium sulfate, filtered and evaporated under reduced pressure to yield g 1.030 (84%) of (3) as a white syrup, which is used for the following step without further purification.

Compound 3 (0.98 g, 4 mmoles) dissolved in 0.1M methanolic sodium methoxide (70 ml) was kept at room temperature. The progress of the reaction was monitored by T.L.C. on silica gel using methylene chloride:methanol (10:1 v/v). When the reaction was complete was neutralized with acetic acid dissolved in methanol and evaporated to give a syrup which was purified by flash chromatography with methylene chloride:methanol (19:1 v/v) gave 0.675 g (83%) of 4 as a syrup.

The PMR spectrum (200 MHz, CHCl$_3$) showed absorption at: 1.33 (d, J=6.2 Hz, 3H, CH$_3$-5), 2.38 (bd, J=7.0 Hz, 1H, OH-4), 3.42 (s, 3H, OCH$_3$), 3.76 (dq, J=9.1, 6.2 Hz, 1H, H-5), 3.99 (ddd, J=9.1, 7.0, 2.0 Hz, 1H, H-4), 4.86, 5.30 (two d, J=13.3 Hz, 2H, CH$_2$NO$_2$), 4.84 (d, J=3.0 Hz, 1H, H-1), 5.90 (dd, J=3.0, 2.0 Hz, 1H, H-2)δ.

EXAMPLE 3

Preparation of methyl 2,3,6-trideoxy-3-trifluoroacetamido methyl-α-L-ribo-hexopyranoside (5) and methyl 2,3,6-trideoxy-3-trifluoroacetamidomethyl-α-L-arabino-hexopyranoside (6)

Compound (4) (0.61 g, 3 mmoles) in 50 ml of water was hydrogenated in the presence of 0.6 g of neutral Raney Nickel under a pressure of 10 atmospheres.

After removal of the catalyst by filtration the pH of the solution was adjusted to pH 6 with aqueous hydrogen chloride and evaporated. The residue was treated with several portions of toluene followed by subsequent evaporation to yield a colorless syrup which was suspended in 20 ml of methylene dichloride and treated with 4 ml of trifluoroacetic anhydride at 0° C.

After 2 hours the reaction mixture was evaporated to dryness and treated with methanol (20 ml). After standing at room temperature the reaction mixture was evaporated to dryness. The TLC of the residue with methylene dichloride:methanol 10:1 as developed, showed the presence of two products with Rf 0.45 and Rf 0.40.

The resulting residue was purified by flash chromatography using methylene chloride:methanol 97.3 as eluting system. There were obtained 0.55 g (67%) of 5;

the PMR spectrum showed absorption at: 1.24 (d, 3H, CH$_3$-5), 1.71 (ddd, J=2.7, 5.0, 14.5 Hz, 1H, H-2ax), 1.87 (ddd, J=4.1, 5.5, 14.5 Hz, 1H, H-2e), 2.21 (m, 1H, H-3), 3.32 (s, 3H, OCH$_3$), 3.53 (dd, J=4.7, 8.1 Hz, 1H, H-4), 3.60 (m, 2H, CH$_2$NH), 3.80 (qd, J=6.4, 8.1 Hz, 1H, H-5), 4.61 (dd, J=2.7, 4.1 Hz, 1H, H-1)δ; FD-MS 271 (M+·) and 0.185 g (23%) of 6.

The PMR spectrum showed absorption at: 1.26 (d, J=6.3, 3H, CH$_3$-5), 1.50 (ddd, J=3.6, 13.5, 13.5 Hz, 1H, H-2ax), 1.80 (ddd, J=1.3, 4.1, 13.5 Hz, 1H, H-2e), 2.0-2.2 (m, 1H, H-3), 2.29 (d, J=5.1 Hz, 1H, OH-4), 3.0-3.1 (m, 1H, CH(H)-NH), 3.06 (ddd, J=5.1, 9.3, 9.6 Hz, 1H, H-4), 3.34 (s, 3H, OCH$_3$), 3.64 (dq, J=6.3, 9.3 Hz, 1H, H-5), 3.76 (ddd, J=3.8, 8.0, 14.0 Hz, 1H, CH(H)—NH), 4.67 (dd, J=1.3, 3.6 Hz, 1H, H-1)δ. FD-MS 271 (M+·).

EXAMPLE 4

Preparation of methyl-4-tert-butyldimethylsilyl-3-(hydroxymethyl)-2,3,6-trideoxy-α-L-ribo-hexopyranoside (9)

3.16 g of methyl 2,3,6-Trideoxy-3-C-methylene-α-L-erythrohexopyranoside (7) dissolved in 30 ml of N,N-dimethylformamide was added with 3.650 g of tert-butyldimethylsilyl chloride and 3.27 g of imidazole at 35° C. for 10 hours.

The reaction mixture was poured into ice-water and extracted with dichloromethane. The extract was washed with water, then dried over sodium sulphate and evaporated under reduced pressure to yield 4.850 g (89%) of 8 as syrup. g 4.5 (16.5 mmoles) of 8 in 30 ml of anhydrous tetrahydrofuran under nitrogen atmosphere, was treated with 27 ml of an anhydrous tetrahydrofuran solution of 1M borane-tetrahydrofuran complex at 0° C.

The solution was stirred at room temperature for 3 hours cooled again and treated with 20 ml of tetrahydrofuran: water (1:1) and 25.5 ml of 2N sodium hydroxide and after 10 minutes 20.5 ml of 30% hydrogen peroxide.

The mixture was stirred at room temperature for 2 hours, chilled again, and treated with 50 ml of saturated aqueous sodium thiosulfate to decompose the excess peroxide.

Sodium chloride was added to saturate the aqueous layer, which was separated and extracted with methylene dichloride. The organic layers were dried and evaporated to yield 4.65 g (97%) of 9.

The PMR spectrum showed absorption at : 0.08, 0.09 (two s, 6H, Si(CH$_3$)$_2$, 0.88 (s, 9H, SiC(CH$_3$)$_3$), 1.17 (d, J=6.4 Hz, 3H, CH$_3$-5), 1.86 (m, 2H, CH$_2$-2), 2.20 (m, 1H, H-3), 2.82 (m, 1H, CH$_2$OH), 3.31 (s, 3H, OCH$_3$), 3.55 (dd, J=5.3, 9.2 Hz, 1H, H-4), 3.76 (ddd, J=6.0, 6.9, 12.0 Hz, 1H, CH(H)—OH), 3.90 (qd, J=6.4, 9.2 Hz, 1H, H-5), 4.01 (ddd, J=4.0, 7.0, 12.0 Hz, 1H, CH(H)—OH), 4.58 (t, J=2.9, 1H, H-1)δ.

EXAMPLE 5

Preparation of methyl 3-azidomethyl-4-tert-butyldimethylsilyl-2,3,6-trideoxy-α-L-ribohexopyranoside (11)

2.9 g (10 mmoles) of 9 dissolved in 20 ml of dry pyridine was treated with methanesulfonyl chloride (2 ml) at 0° C. overnight. The mixture was poured into icewater and the aqueous mixture extracted with methylene chloride. The combined organic extract was washed with aqueous hydrogen chloride, aqueous sodium hydrogen carbonate, water and then dried on sodium sulfate. Evaporation of the filtrate gave 3.40 g (92%) of 10. g 3 (8.15 mmoles) of 10 dissolved in 30 ml of dry N,N-dimethylformamide was treated with an excess of sodium azide (3.2 g). The mixture was refluxed for 30' and then poured into ice-water with stirring and product was extracted with methylene dichloride. The resulting syrup was purified by flash chromatography using methylene chloride as eluent; yield 2.50 g (80%) of pure 11.

I.R.: 2110 cm$^-$ (azide).

EXAMPLE 6

Preparation of methyl 2,3,6-trideoxy-3-trifluoroacetamidomethyl-α-L-ribo-hexopyranoside (5)

2.50 g (8 mmoles) of 11 was dissolved in 50 ml of tetrahydrofuran at room temperature. To the solution was added 5 g of tetrabutylammonium fluoride. The solution was stirred for 1 hour and then diluted with methylene dichloride and water.

The aqueous layer was extracted with methylene chloride and combined organic solutions were washed with water, dried (Na$_2$SO$_4$) and concentrated to dryness.

To the syrup dissolved in dry methanol (75 ml) was added 20% Palladium on carbon (1 g), and the mixture was hydrogenated at 10 atms. 3 hours, filtered and concentrated to dryness.

A solution of the resulting syrup in anhydrous methylene chloride (40 ml) at 0° C. was treated with trifluoroacetic anhydride (6 ml). After 2 hours, the mixture was concentrated to dryness. The residue was dissolved in anhydrous methanol (50 ml) overnight. The solvent was removed and the residue was purified by flash chromatography with methylene chloride:methanol 97:3 as eluting system.

There were obtained 1.540 g (71%) of 5.

EXAMPLE 7

Preparation of methyl-4-tert-butyldimethylsilyl-3-formyl-2,3,6-trideoxy-α-L-ribo-hexopyranoside (12)

To 0.5 L ml (5.5 mmoles) of oxalyl chloride dissolved in 15 ml of methylene chloride at −60° C. was added with stirred, 0.85 ml (11 mmoles) of dimethylsulfoxide dissolved in 5 ml of methylene chloride. The reaction mixture was stirred for 5 minutes and then was added 1.45 g (5 mmoles) of 9 dissolved in 10 ml of methylene chloride. After 15 minutes was added 3.5 ml of triethylamine and the reaction mixture was stirred for 5 minutes and then allowed to warm to room temperature. Water (25 ml) was added and the aqueous layers was reextracted with methylene chloride. The organic layer were combined, washed with satured sodium chloride and dried over anhydrous magnesium sulfate and evaporated to yield 1.34 g (93%) of 12.

The PMR spectrum showed adsorption at: 0.03, 0.06 (two s, 6H, Si(CH$_3$)$_2$), 0.84 (s, 9H, SiC(CH$_3$)$_3$), 1.25 (d, J=6.2 Hz, 3H, CH$_3$-5), 1.97 (ddd, J=3.4, 6.0, 14.0 Hz), 1H, H-2ax), 2.09 (ddd, J=1.4, 2.6, 14.0 Hz, 1H, H-2e), 2.54 (dddd, J=3.0, 2.6, 5.6, 6.0 Hz, 1H, H-3), 3.30 (s, 3H, OCH$_3$), 3.54 (dd, J=5.6, 9.7 Hz, 1H, H-4), 4.03 (qd, J=6.2, 9.7 Hz, 1H, H-5), 4.56 (dd, J=1.4, 3.4 Hz, 1H, H-1), 10.02 (d, J=3.0 Hz, 1H, CHO)δ.

EXAMPLE 8

Preparation of methyl 4-tert-butyldimethylsilyl-3-formyl-2,3,6-trideoxy-α-L-arabino-hexopyranoside (13)

1.30 g (4.5 mmoles) of 12 dissolved in 30 ml of dry triethylamine was stirred under reflux.

The progress of the reaction was monitored by t.l.c. on silica gel using 9:1 toluene-acetone as developer. When the reaction was evaporated and the resulting residue was filtered through a short column of silica gel using toluene as the eluent; yield 1.25 g (96%) of 13.

The PMR spectrum showed absorption at: −0.01, 0.08 (two s, 6H, Si(CH$_3$)$_2$), 0.86 (s, 9H, SiC(CH$_3$)$_3$), 1.22 (d, J=6.2 Hz, 3H, CH$_3$-5), 1.6–1.9 (m, 2H, CH$_2$-2), 2.93 (dddd, J=2.5, 5.0, 9.2, 12.0 Hz, 1H, H-3) 3.33 (s, 3H, OCH$_3$), 3.51 (dd, J=9.2, 9.2 Hz, 1H, H-4), 3.66 (qd, J=6.2, 9.2 Hz, 1H, H-5), 4.58 (dd, J=1.5, 3.5 Hz, 1H, H-1), 9.77 (d, J=2.5 Hz, 1H, CHO)δ.

EXAMPLE 9

Preparation of methyl 4-tert-butyldimethylsilyl-3-hydroxymethyl-2,3,6-trideoxy-α-L-arabino-hexopyranoside (14)

1.2 g (4.15 mmoles) of 13 dissolved in 50 ml of methanol was reduced with sodium borohydride (0.1 g) at 0° C. for 20 minutes. The excess sodium borohydride was consumed by the addition of acetone. After addition of 25 ml of water the solution was neutralized with acetic acid and then extracted with methylene chloride. The organic extracts were evaporated to dryness to give 1.2 g (100%) of 14.

The PMR spectrum showed absorption at: 0.08, 0.09 (two s, 6H, Si(CH$_3$)$_2$), 0.88 (s, 9H, SiC(CH$_3$)$_3$), 1.20 (d, J=6.3 Hz, 3H, CH$_3$-5), 1.66 (ddd, J=3.6, 13.0, 1H, H-2ax), 1.85 (ddd, J=1.4, 2.5; 13.0 Hz, 1H, H-2e), 1.9–2.0 (m, 1H, H-3), 3.22 (dd, J=9.4, 9.4 Hz, 1H, H-4), 3.33 (s, 3H, OCH$_3$), 3.6–3.7 (m, 3H, H-5, CH$_2$OH), 4.68 (dd, J=1.4, 3.6 Hz, 1H, H-1)δ.

EXAMPLE 10

Preparation of methyl 2,3,6-trideoxy-3-trifluoroacetamidomethyl-α-L-arabino-hexopyranoside (6)

The synthesis of the title compound, starting from 14, via mesylation followed by azidolysis was prepared following the procedure described in examples 5 and 6.

EXAMPLE 11

Preparation of 2,3,6-trideoxy-3-trifluoroacetamidomethyl-4-trifluoroacetyl-α-L-ribo-hexopyranosyl chloride (III-A)

A solution of 0.5 g (1.84 mmoles) of 5 in 10 ml of acetic acid and 40 ml of water was reacted at 100° C. for 1 hour. The solution was evaporated under vacuum. The residue was dissolved in 25 ml of methylene dichloride and treated at 0° C. with 3 ml of trifluoroacetic anhydride. After two hours at 0° C. and 1 hour at room temperature, the reaction mixture was evaporated as a syrup which was directly dissolved in 15 ml of anhydrous diethyl ether. The solution was saturated at 0° C. with dry hydrogen chloride.

After standing at 0° C. overnight, the reaction mixture was evaporated in vacuum to give the title compound suitable for the subsequent reaction without further purification.

EXAMPLE 12

Preparation of 3'-desamino-3'-aminomethyl-3',4'-epi-daunorubicin (I-A)

To a solution of daunomycinone (0.004 g, 1 mmole) in 50 ml of anhydrous methylene dichloride there was added 2,3,6-trideoxy-3-trifluoroacetamidomethyl-4-trifluoroacetyl-L-ribohexopyranosyl chloride (0.37 g, 1 mmole) prepared as described in Example 11 in 15 ml of methylene dichloride and 4 g of molecular sieve (4 Å, Merck). The mixture was then treated with 0.28 g of silver trifluoromethanesulphonate in 15 ml of an hydrous diethyl ether under vigorous stirring.

After 15 minutes the reaction mixture was treated with a saturated aqueous solution of sodium hydrogen carbonate. The separated organic phase was washed with water and then evaporated to dryness.

The solid residue was dissolved in dry methanol (25 ml) and kept overnight. The crude product obtained by evaporating the solvent was chromatographed over a column of silica gel, using methylene dichloride:acetone=19:1 as the eluting agent, to give pure 3'-desamino-3'-trifluoroacetamidomethyl-3',4'-epi-daunorubicin (0.410 g, 63%): m.p. 161°–163° C.

The PMR spectrum showed absorption at: 1.30 (d, J=6.1 Hz, 3H, CH$_3$-5'), 1.7–2.5 (m, 5H, CH$_2$-8, CH$_2$-2', CH-3'), 2.41 (s, 3H, COCH$_3$), 2.88 (d, J=18.9 Hz, 1H, H-10ax), 3.18 (dd, J=1.5, 18.9 Hz, 1H, H-10e), 3.4–3.8 (m, 3H, CH$_2$-NH, H-5'), 4.07 (s, 3H, OCH$_3$-4), 4.53 (s, 1H, OH-9), 5.23 (m, 1H, H-7), 5.29 (dd, J=<1, 5.0 Hz, 1H, H-1'), 7.38 (d, J=8.3 Hz, 1H, H-3), 7.76 (dd, J=8.3, 8.3 Hz, 1H, H-2), 8.01 (d, J=8.3 Hz, 1H, H-1), 13.26 (s, 1H, OH-11), 13.97 (s, 1H, OH-6)δ.

A solution of 0.4 g of the above named compound in 10 ml of acetone was treated with 40 ml of 0.1N aqueous sodium hydroxide and stirred under nitrogen at 15° C. After 1 hour the reaction mixture was adjusted to pH 3.5 with 1N aqueous hydrogen chloride and then extracted with methylene dichloride to eliminate impurities.

The aqueous phase, adjusted to pH 8.0 was extracted with methylene dichloride.

The combined organic extracts were dried over sodium sulphate, concentrated to a small volume and acidified to pH 4.5 with 0.25N methanolic hydrogen chloride. Addition of excess diethyl ether gave 3'-desamino-3'-aminomethyl-3',4'-epi-daunorubicin (I-A) as the hydrochloride (0.300 g) m.p. 151°–153° C. (with decomposition.

EXAMPLE 13

Preparation of 3'-desamino-3'-aminomethyl-3',4'-epi-doxorubicin (I-B)

A solution of 0.200 g of 3'-desamino -3'-aminomethyl-3',4'-epi-daunorubicin hydrochloride (I-A) prepared as described in Example 12, in a mixture of 3 ml of anhydrous methanol, 8 ml of dioxan and 0.2 ml of ethyl orthoformate was treated with 0.45 ml of a solution containing 0.95 g of bromine in 10 ml of methylene dichloride.

After 1.5 hours at 15° C., the reaction mixture was poured into a mixture of 40 ml of diethyl ether and 40 ml of petroleum ether.

The resultant red precipitate, after being filtered off and washed with diethyl ether, was dissolved in a mixture of 7.5 ml of acetone and 7.5 ml of 0.25N aqueous hydrogen bromide. After one day at 30° C., the reaction mixture was treated with 0.35 g of sodium formate in 4 ml of water and stirred at 30° C. for 2 days.

The reaction mixture was extracted with methylene dichloride in order to remove some lipophilic impurities. The aqueous phase, after being adjusted to pH 7.6 with aqueous sodium bicarbonate, was repeatedly extracted with methylene dichloride.

The combined organic extracts were dried over sodium sulphate and evaporated to a small volume under vacuum. To the resulting red solution, adjusted to pH 3.5 with anhydrous methanolic hydrogen chloride, excess diethyl ether was added to give 3'-desamino-3'-aminomethyl-3',4'-epi-doxorubicin (I-B, 0.180 g).

EXAMPLE 14

Preparation of 2,3,6-trideoxy-3-trifluoroacetamidomethyl-4-trifluoroacetyl-L-arabino-hexopyranosyl chloride (III-B)

The synthesis of the title compound, starting from $\underline{6}$, was carried out according to the procedure described in Example 11.

EXAMPLE 15

Preparation of 3'-desamino-3'-aminomethyl-4'-epi-daunorubicin (1-C)

The synthesis of the title compound starting from daunomycinone and 2,3,6-trideoxy-3-trifluoroacetamidomethyl-4-trifluoroacetyl-L-arabino-hexopyranosyl chloride (III-B) was carried out according to the procedure described in Example 12.

The Pmr spectrum of the 3'-desamino-3'-trifluoroacetamidomethyl-3',4'-epi-daunorubicin showed absorption at 1.32 (d, J=6.0 Hz, 3H, $\underline{CH_3}$-5'), 1.5–1.9 (m, 3H, $\underline{CH_2}$-2'; $\underline{H-3'}$), 2.0–2.4 (m, 2H, $\underline{CH_2}$-8), 2.42 (s, 3H, CO$\underline{CH_3}$), 2.64 (d, J=5.3 Hz, 1H, $\underline{OH}$-4), 2.94 (d, J=18.9 Hz, 1H, $\underline{H-10ax}$), 3.05 (m, 1H, $\underline{H-4'}$), 3.23 (dd, J=1.5, 18.9 Hz, 1H, $\underline{H-10e}$), 3.6–3.8 (m, 2H, $\underline{CH_2}$—NH), 3.87 (qd, J=6.0, 9.2 Hz, 1H, $\underline{H-5'}$) 4.08 (s, 3H, O$\underline{CH_3}$-4), 4.59 (s, 1H, $\underline{OH}$-9), 5.30 (dd, J=1.9, 3.7 Hz, 14, $\underline{H-7}$), 5.45 (dd, J<1, 3.5 Hz, 1H, $\underline{H-1'}$), 7.25 (m, 1H, $\underline{NH}$—COCF$_3$), 7.39 (d, J=8.1 Hz, 1H, $\underline{H-3}$), 7.78 (dd, $\overline{J=8.1}$, 8.1 Hz, 1H, $\underline{H-2}$), 8.03 (d, J=8.1 Hz, 1H, $\underline{H-1}$), 13.28 (s, 1H, $\underline{OH}$-11), 14.00 (s, 1H, $\underline{OH}$-6)δ.

3'-desamino-3'-aminomethyl-4'-epi-daunorubicin (I-C) was obtained as the hydrochloride in the form of red crystals, m.p. 164°–165° (with decomposition).

EXAMPLE 16

Preparation of 3'-desamino-3'-aminomethyl-4'-epi-doxorubicin (I-D)

Compound I-C prepared as described in Example 15, was transformed into the corresponding 14-hydroxy derivative, according to the procedure described in Example 13.

3'-Desamino-3'-aminomethyl-4'-epi-doxorubicin (I-D) was obtained as the hydrochloride in the form of red crystals, m.p. 170°–172° C. with decomposition.

Biological activity of IB

Compound IB has been tested in comparison with daunorubicin (DNR) against HeLa and P388 cells in vitro (Table 1).

The in vivo effect of IB against disseminated Gross leukemia is reported in Table 2. Here, IB, administered iv, was less potent than DNR; however, the new compound at the maxima tolerated dose (32.11 mg/Kg) was more active than DNR (MxTD=15 mg/Kg).

TABLE 1

Cytotoxic activity of IB in comparison with daunorubicin

| COMPOUND | ID$_{50}$ (NG/ML) | |
|---|---|---|
|  | HeLa+ | P388++ |
| DNR | 10.5 | 8.4 |
| IB | 6.4 | 10 |

+COLONY INHIBITION TEST AFTER 24 HOURS EXPOSURE TO THE DRUGS.
++CYTOTOXICITY EVALUATED AFTER 48 HOURS EXPOSURE TO THE DRUGS BY CELL COUNTING TECHNIQUE.

TABLE 2

EFFECT AGAINST GROSS LEUKEMIA$^{(A)}$

| COMPOUND | DOSE$^{(B)}$ MG/KG | T/C %$^{(C)}$ | TOXIC$^{(D)}$ DEATHS |
|---|---|---|---|
| DNR | 10 | 150 | 0/10 |
|  | 15 | 183 | 0/10 |
|  | 22.5 | 217 | 2/10 |
| IB | 19 | 167 | 0/10 |
|  | 24.7 | 183 | 0/10 |
|  | 32.11 | 200 | 1/10 |

$^{(A)}$EXPERIMENTS WERE PERFORMED IN C3H MICE, INOCULATED WITH 2 × 10$^6$ LEUKEMIA CELLS I.V.
$^{(B)}$TREATMENT I.V. ON DAY 1 AFTER TUMOR INOCULUM.
$^{(C)}$MEDIAN SURVIVAL TIME OF TREATED MICE/MEDIAN SURVIVAL TIME OF CONTROLS × 100
$^{(D)}$EVALUATED ON THE BASIS OF AUTOPSY FINDINGS.

We claim:

1. An anthracycline of the formula (I):

wherein R$^1$ is hydrogen or hydroxy and either R$^2$ or R$^3$ is hydrogen with the other being —CH$_2$NH$_2$, and pharmaceutically acceptable addition salts thereof.

2. A compound according to claim 1, which is 3'-desamino-3'-aminomethyl-3',4'-epi-daunorubicin or the hydrochloride thereof.

3. A compound according to claim 1, which is 3'-desamino-3'-aminomethyl-3',4'-epi-doxorubicin or the hydrochloride thereof.

4. A compound according to claim 1, which is 3'-desamino-3'-aminomethyl-4'-epi-daunorubicin or the hydrochloride thereof.

5. A compound according to claim 1, which is 3'-desamino-3'-aminomethyl-4'-epi-doxorubicin or the hydrochloride thereof.

6. 2,3,6-Trideoxy-3-trifluoroacetamidomethyl-4-trifluoroacetyl-L-ribo-hexopyranosyl chloride of formula (III-A):

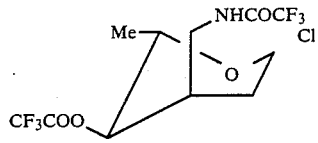

7. 2,3,6-Trideoxy-3-trifluoroacetamidomethyl-4-trifluoroacetyl-L-arabino-hexopyranosyl chloride of formula (III-B):

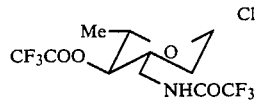

8. A pharmaceutical composition for inhibiting the growth of a tumor selected from the group consisting of P 388 leukemia and Gross leukemia comprising a therapeutically effective amount of the anthracycline glycoside or pharmaceutically acceptable salt thereof of claim 1 in admixture with a pharmaceutically acceptable diluent or carrier.

* * * * *